(12) United States Patent
Morris

(10) Patent No.: US 10,639,428 B2
(45) Date of Patent: May 5, 2020

(54) INSERT AND DRUG DELIVERY DEVICE HEREWITH

(71) Applicant: Sanofi, Paris (FR)

(72) Inventor: Anthony Paul Morris, Coventry (GB)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 15/517,251

(22) PCT Filed: Oct. 9, 2015

(86) PCT No.: PCT/EP2015/073434
§ 371 (c)(1),
(2) Date: Apr. 6, 2017

(87) PCT Pub. No.: WO2016/055628
PCT Pub. Date: Apr. 14, 2016

(65) Prior Publication Data
US 2017/0304554 A1    Oct. 26, 2017

(30) Foreign Application Priority Data

Oct. 9, 2014 (EP) .................................. 14306588

(51) Int. Cl.
*A61M 5/315* (2006.01)
*A61M 5/20* (2006.01)
*A61M 5/31* (2006.01)

(52) U.S. Cl.
CPC .......... *A61M 5/31583* (2013.01); *A61M 5/20* (2013.01); *A61M 5/31528* (2013.01);
(Continued)

(58) Field of Classification Search
CPC .......... A61M 5/31583; A61M 5/31593; A61M 5/20; A61M 5/31528; A61M 5/31553;
(Continued)

(56) References Cited

U.S. PATENT DOCUMENTS

| | | | | |
|---|---|---|---|---|
| 2004/0210199 A1* | 10/2004 | Atterbury | ......... | A61M 5/31535 604/224 |
| 2010/0114025 A1* | 5/2010 | Moller | ................... | A61M 5/20 604/135 |

(Continued)

FOREIGN PATENT DOCUMENTS

| | | |
|---|---|---|
| AU | 2008 231 897 | 10/2008 |
| CA | 2 594 764 | 7/2006 |

(Continued)

OTHER PUBLICATIONS

International Preliminary Report on Patentability in International Application No. PCT/EP2015/073434, dated Apr. 11, 2017, 8 pages.

(Continued)

*Primary Examiner* — Andrew M Gilbert
(74) *Attorney, Agent, or Firm* — Fish & Richardson P.C.

(57) ABSTRACT

The present disclosure is generally directed to a drug delivery device for selecting and dispensing a number of user variable doses of a medicament and to an insert for such a device. The insert comprises a cup-shaped body with a distal end and a proximal end. The body has a sidewall and a tube which extends centrally through the cup-shaped body in a longitudinal direction, thereby defining an annular space between the sidewall and the tube. The annular space is open in the proximal direction for receiving a compression spring. The tube comprises a thread provided at an inner surface of the tube. Further, the tube, the sidewall and/or a second part comprise a clutch feature for rotationally constraining a component part to the insert.

13 Claims, 3 Drawing Sheets

Specification includes a Sequence Listing.

(52) U.S. Cl.
CPC .... *A61M 5/31541* (2013.01); *A61M 5/31553* (2013.01); *A61M 5/31593* (2013.01); *A61M 2005/2026* (2013.01); *A61M 2005/3126* (2013.01); *A61M 2205/58* (2013.01)

(58) Field of Classification Search
CPC .......... A61M 5/31533; A61M 5/31535; A61M 5/3155; A61M 5/31551; A61M 5/31585
See application file for complete search history.

(56) References Cited

U.S. PATENT DOCUMENTS

| | | | |
|---|---|---|---|
| 2011/0054412 A1 | 3/2011 | Eich et al. | |
| 2013/0053789 A1* | 2/2013 | Harms | A61M 5/24 604/211 |
| 2015/0100029 A1* | 4/2015 | Cowe | A61M 5/20 604/218 |
| 2016/0206826 A1* | 7/2016 | Bilton | A61M 5/20 |
| 2016/0256631 A1* | 9/2016 | Soerensen | A61M 5/24 |

FOREIGN PATENT DOCUMENTS

| | | |
|---|---|---|
| CN | 101641126 | 2/2010 |
| CN | 103167890 | 6/2013 |
| JP | 2006-187628 | 7/2006 |
| JP | 2008-529625 | 8/2008 |
| JP | 2010-521275 | 6/2010 |
| JP | 2012-148198 | 8/2012 |
| JP | 2012-528631 | 11/2012 |
| JP | 2013-542801 | 11/2013 |
| WO | WO 2006/069454 | 7/2006 |
| WO | WO 2006/084876 | 8/2006 |
| WO | WO 2007/063342 | 6/2007 |
| WO | WO 2008/116766 | 10/2008 |
| WO | WO 2010/139643 | 12/2010 |
| WO | WO 2011/060785 | 5/2011 |
| WO | WO 2012/049138 | 4/2012 |
| WO | WO 2012/063061 | 5/2012 |
| WO | WO 2012/125876 | 9/2012 |
| WO | WO 2013/119132 | 8/2013 |
| WO | WO 2014/033197 | 3/2014 |

OTHER PUBLICATIONS

International Search Report and Written Opinion in International Application No. PCT/EP2015/073434, dated Dec. 14, 2015, 11 pages.

* cited by examiner

INSERT AND DRUG DELIVERY DEVICE HEREWITH

CROSS-REFERENCE TO RELATED APPLICATIONS

This application is a U.S. national stage application under 35 USC § 371 of International Application No. PCT/EP2015/073434, filed on Oct. 9, 2015, which claims priority to European Patent Application No. 14306588.6, filed on Oct. 9, 2014, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Dec. 11, 2019, is titled "Sequence_Listing.txt," and has a size of 28.0 KB.

TECHNICAL FIELD

The present disclosure is generally directed to an insert, e.g. a housing insert, for a drug delivery device and to a drug delivery device for selecting and dispensing a number of user variable doses of a medicament comprising such a housing.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. Some embodiments may be directed to reusable devices which allow resetting of the device and a replacement of a cartridge. Resetting of the device typically involves moving a piston rod or lead screw from an extended (distal) position, i.e. a position after dose dispensing, into a more retracted (proximal) position.

These types of pen delivery devices (so named because they often resemble an enlarged fountain pen) generally comprise three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

SUMMARY

In certain aspects, an insert comprises a cup-shaped body with a distal end and a proximal end. The body has a sidewall and a tube which extends centrally through the cup-shaped body in the longitudinal direction defining an annular space between the sidewall and the tube. This space is open in the proximal direction for receiving a compression spring. The tube comprises a thread provided at its inner surface, e.g. for engaging a threaded piston rod. Further, the tube, the sidewall and/or a separate, e.g. ring-shaped, part comprise a clutch feature for rotationally constraining a component part, e.g. a drive sleeve, to the insert. In other words, the insert comprises various interfaces for engagement and/or interaction with further component parts of a drug delivery device. An insert having multiple functions contributes in minimizing the number of component parts required for a drug delivery device. In addition, the lower number of parts facilitates assembly.

A drug delivery device for selecting and dispensing a number of user variable doses of a medicament comprises a housing, the insert which is rotationally and/or axially constrained to the housing, a cartridge holder and a cartridge containing a medicament. Further, a drug delivery device may comprise a piston rod, a drive member, a nut, a dose setting element, a button, a dose setting grip, a drive spring, a gauge element, a clutch and/or a clutch spring.

The annular space between the sidewall and the tube of the insert preferably defines a portion for receiving and/or guiding an axially displaceable component part, like a movable drive sleeve. A drug delivery device may comprise a drive member (drive sleeve) which is preferably an axially displaceable tubular element at least partly surrounding a piston rod, with the distal end of the drive member having an inner diameter being equal to or larger than the outer diameter of the tube of the insert and an outer diameter being equal to or smaller than the inner diameter of the sidewall of the insert. This allows the drive member to be introduced into the annular space between the sidewall and the tube depending on the axial position of the drive member relative to the insert. In a preferred embodiment the axial position of the drive member relative to the insert defines a state of the device, for example a dose setting (or dose correcting) state and a dose dispensing state. The drive member may be rotationally locked to the insert by the clutch feature for dose setting while being allowed to rotate relative to the insert during dose dispensing. For example, the drive member comprises axially extending splines provided at its outer surface and the clutch feature of the insert comprises corresponding axially extending splines provided at the inner surface of the sidewall of the insert. This allows coupling and decoupling of the drive member to and from the insert depending on the relative axial position of the drive member and the insert.

In a further embodiment the piston rod has an outer diameter being equal to or smaller than the inner diameter of the tube of the insert and comprises an outer thread for engaging the thread of the tube. In other words, the piston rod is guided in the tube of the insert such that rotation of the piston rod relative to the insert causes an axial displacement of the piston rod relative to the insert. This axial movement of the piston rod may be used to expel medicament from the cartridge. The rotation of the piston rod may be caused by a rotation of the drive member, which is preferably splined to the piston rod to allow relative axial movement while preventing relative rotational movement.

The annular space between the sidewall and the tube of the insert has the further function of retaining a spring, preferably a clutch spring. The clutch spring may be a compression spring located within the annular space interposed between the insert and the drive member. The insert tube may position the spring radially. Preferably, the clutch spring has the additional function of biasing the drive member into its axial dose setting (or dose correcting) position, i.e. into a position where the corresponding spline teeth on the insert and the drive member engage.

The insert may further comprise at least one, e.g. splined, arm extending radially outwards from the sidewall. This arm preferably locks the insert to the housing or a further fixed-point of the drug delivery device. For example, the at least one arm comprises a permanent or releasable clutch feature for rotationally and/or axially constraining the insert to a further component part. As an alternative, the insert may be integrally connected to the housing by the at least one arm to form one single component part with the housing.

As a further alternative, the insert may be partially formed as one single component part with the housing and partially as a separate component part. For example, the cup-shaped body and the threaded tube may be one single component part with the housing, whereas the clutch feature for rotationally constraining a component part, like the drive sleeve, to the insert may be a separate, e.g. ring-shaped, component part which is at least rotationally constrained to the housing. In a preferred embodiment, the ring-shaped insert part comprises axially orientated splines on an inner surface to rotationally restrain the drive sleeve. For example, the ring-shaped insert part may comprise arms and/or splines for rotational retention within the portion of the insert which is integrally connected to the housing and/or within the housing itself. Further, at least one snap clip, e.g. a hook-like arm, may be provided for axial retention of the ring-shaped insert part within the portion of the insert which is integrally connected to the housing and/or within the housing itself.

The ring-shaped insert part preferably comprises a hole and/or a pocket for receiving and fixing a hook end of the drive spring.

A further function of the insert may be to provide a fixation for a drive spring. The drive spring is preferably a torsion spring having at least at its distal end a hook engaging an opening of the insert. For example, the proximal end of the sidewall and/or the at least one arm comprises an axially extending opening for receiving a hook end of the drive spring.

The cup-shaped body of the insert may comprise a radially extending bottom wall closing the annular space at the distal end. This may provide a force reaction face for the clutch spring. The distal end of the tube is preferably flush with the bottom wall. The axial length of the insert tube may be larger than the axial length of the sidewall. As an alternative, the sidewall may be longer than or as long as the tube.

The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe- Ile-Glu-Trp-Leu-Lys-Asn-Gly-Gly-Pro-Ser-Ser-Gly-Ala-Pro-Pro-Pro-Ser-NH2 (SEQ ID NO:1).

Exendin-4 derivatives are for example selected from the following list of compounds:

(SEQ ID NO: 2)
H-(Lys)4-des Pro36, des Pro37 Exendin-4(1-39)-NH2, (SEQ ID NO: 3)
H-(Lys)5-des Pro36, des Pro37 Exendin-4(1-39)-NH2, (SEQ ID NO: 4)
des Pro36 Exendin-4(1-39), (SEQ ID NO: 5)
des Pro36 [Asp28] Exendin-4(1-39), (SEQ ID NO: 6)
des Pro36 [IsoAsp28] Exendin-4(1-39), (SEQ ID NO: 7)
des Pro36 [Met(O)14, Asp28] Exendin-4(1-39), (SEQ ID NO: 8)
des Pro36 [Met(O)14, IsoAsp28] Exendin-4(1-39), (SEQ ID NO: 9)
des Pro36 [Trp(O2)25, Asp28] Exendin-4(1-39), (SEQ ID NO: 10)
des Pro36 [Trp(O2)25, IsoAsp28] Exendin-4(1-39), (SEQ ID NO: 11)
des Pro36 [Met(O)14 Trp(O2)25, Asp28] Exendin-4 (1-39), (SEQ ID NO: 12)
des Pro36 [Met(O)14 Trp(O2)25, IsoAsp28] Exendin-4 (1-39);
or (SEQ ID NO: 5)
des Pro36 [Asp28] Exendin-4(1-39), (SEQ ID NO: 6)
des Pro36 [IsoAsp28] Exendin-4(1-39), (SEQ ID NO: 7)
des Pro36 [Met(O)14, Asp28] Exendin-4(1-39), (SEQ ID NO: 8)
des Pro36 [Met(O)14, IsoAsp28] Exendin-4(1-39), (SEQ ID NO: 9)
des Pro36 [Trp(O2)25, Asp28] Exendin-4(1-39), (SEQ ID NO: 10)
des Pro36 [Trp(O2)25, IsoAsp28] Exendin-4(1-39), (SEQ ID NO: 11)
des Pro36 [Met(O)14 Trp(O2)25, Asp28] Exendin-4 (1-39), (SEQ ID NO: 12)
des Pro36 [Met(O)14 Trp(O2)25, IsoAsp28] Exendin-4(1-39), wherein the group -Lys6-NH2 may be bound to the C-terminus of the Exendin-4 derivative;
or an Exendin-4 derivative of the sequence (SEQ ID NO: 13)
des Pro36 Exendin-4(1-39)-Lys6-NH2 (AVE0010), (SEQ ID NO: 14)
H-(Lys)6-des Pro36 [Asp28] Exendin-4(1-39)-Lys6-NH2, (SEQ ID NO: 15)
des Asp28 Pro36, Pro37, Pro38Exendin-4(1-39)-NH2, (SEQ ID NO: 16)
H-(Lys)6-des Pro36, Pro38 [Asp28] Exendin-4(1-39)-NH2, (SEQ ID NO: 17)
H-Asn-(Glu)5des Pro36, Pro37, Pro38 [Asp28] Exendin-4(1-39)-NH2, (SEQ ID NO: 18)
des Pro36, Pro37, Pro38 [Asp28] Exendin-4(1-39)-(Lys)6-NH2, (SEQ ID NO: 19)
H-(Lys)6-des Pro36, Pro37, Pro38 [Asp28] Exendin-4(1-39)-(Lys)6-NH2, (SEQ ID NO: 20)
H-Asn-(GLu)5-des Pro36, Pro37, Pro38 [Asp28] Exendin-4(1-39)-(Lys)6-NH2, (SEQ ID NO: 21)
H-(Lys)6-des Pro36 [Trp(O2)25, Asp28] Exendin-4(1-39)-Lys6-NH2, (SEQ ID NO: 22)
H-des Asp28 Pro36, Pro37, Pro38 [Trp(O2)25] Exendin-4(1-39)-NH2, (SEQ ID NO: 23)
H-(Lys)6-des Pro36, Pro37, Pro38 [Trp(O2)25, Asp28] Exendin-4(1-39)-NH2, (SEQ ID NO: 24)
H-Asn-(Glu)5-des Pro36, Pro37, Pro38 [Trp(O2)25, Asp28] Exendin-4(1-39)-NH2, (SEQ ID NO: 25)
des Pro36, Pro37, Pro38 [Trp(O2)25, Asp28] Exendin-4(1-39)-(Lys)6-NH2, (SEQ ID NO: 26)
H-(Lys)6-des Pro36, Pro37, Pro38 [Trp(O2)25, Asp28] Exendin-4(1-39)-(Lys)6-NH2, (SEQ ID NO: 27)
H-Asn-(GLu)5-des Pro36, Pro37, Pro38 [Trp(O2)25, Asp28] Exendin-4(1-39)-(Lys)6-NH2, (SEQ ID NO: 28)
H-(Lys)6-des Pro36 [Met(O)14, Asp28] Exendin-4(1-39)-Lys6-NH2, (SEQ ID NO: 29)
des Met(O)14 Asp28 Pro36, Pro37, Pro38 Exendin-4(1-39)-NH2, (SEQ ID NO: 30)
H-(Lys)6-desPro36, Pro37, Pro38 [Met(O)14, Asp28] Exendin-4(1-39)-NH2, (SEQ ID NO: 31)
H-Asn-(Glu)5-des Pro36, Pro37, Pro38 [Met(O)14, Asp28] Exendin-4(1-39)-NH2, (SEQ ID NO: 32)
des Pro36, Pro37, Pro38 [Met(O)14, Asp28] Exendin-4(1-39)-(Lys)6-NH2, (SEQ ID NO: 33)
H-(Lys)6-des Pro36, Pro37, Pro38 [Met(O)14, Asp28] Exendin-4(1-39)-(Lys)6-NH2, (SEQ ID NO: 34)
H-Asn-(Glu)5 des Pro36, Pro37, Pro38 [Met(O)14, Asp28] Exendin-4(1-39)-(Lys)6-NH2, -continued

```
                                              (SEQ ID NO: 35)
H-Lys6-des Pro36 [Met(O)14, Trp(O2)25, Asp28]
Exendin-4(1-39)-Lys6-NH2, (SEQ ID NO: 36)
H-des Asp28 Pro36, Pro37, Pro38 [Met(O)14,
Trp(O2)25] Exendin-4(1-39)-NH2, (SEQ ID NO: 30)
H-(Lys)6-des Pro36, Pro37, Pro38 [Met(O)14, Asp28]
Exendin-4(1-39)-NH2, (SEQ ID NO: 37)
H-Asn-(Glu)5-des Pro36, Pro37, Pro38 [Met(O)14,
Trp(O2)25, Asp28] Exendin-4(1-39)-NH2, (SEQ ID NO: 38)
des Pro36, Pro37, Pro38 [Met(O)14, Trp(O2)25,
Asp28] Exendin-4(1-39)-(Lys)6-NH2, (SEQ ID NO: 39)
H-(Lys)6-des Pro36, Pro37, Pro38 [Met(O)14,
Trp(O2)25, Asp28] Exendin-4(S1-39)-(Lys)6-NH2, (SEQ ID NO: 40)
H-Asn-(Glu)5-des Pro36, Pro37, Pro38 [Met(O)14,
Trp(O2)25, Asp28] Exendin-4(1-39)-(Lys)6-NH2;
``` or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra-low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three on the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

Non-limiting, exemplary embodiments will now be described with reference to the accompanying drawings, in which:

FIG. 5b shows a detail of the embodiment of FIG. 5a.

DETAILED DESCRIPTION

Figure 1:
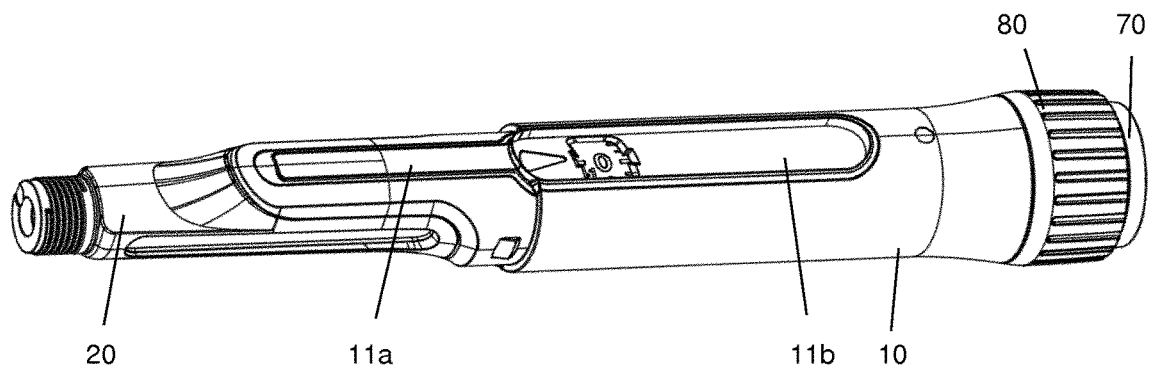
FIG. 1 shows a top view of a drug delivery device according to a first embodiment.
Figure 2:
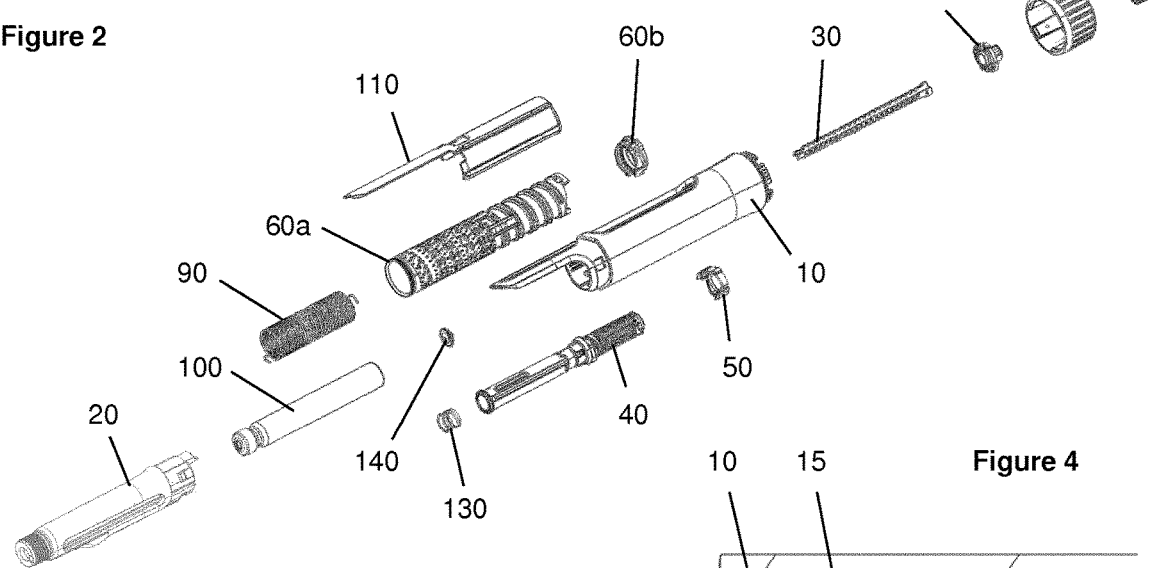
FIG. 2 shows an exploded view of the components of the device of FIG. 1.

FIG. 1 shows a drug delivery device in the form of an injection pen. The device has a distal end (left end in FIG. 1) and a proximal end (right end in FIG. 1). The component parts of the drug delivery device are shown in FIG. 2. The drug delivery device comprises a body or housing 10, a cartridge holder 20, a lead screw (piston rod) 30, a drive sleeve 40, a nut 50, a dose indicator (number sleeve) 60, a button 70, a dial grip or dose selector 80, a torsion spring 90, a cartridge 100, a gauge element 110, a clutch plate 120, a clutch spring 130 and a bearing 140. A needle arrangement (not shown) with a needle hub and a needle cover may be provided as additional components, which can be exchanged as explained above. All components are located concentrically about a common principal axis I (FIG. 3b) of the mechanism.

The housing 10 or body is a generally tubular casing element having a proximal end with an enlarged diameter. The housing 10 provides location for the liquid medication cartridge 100 and cartridge holder 20. As shown in FIGS. 1 and 2, the housing comprises a first window 11a and a second window (or lens) 11b which are incorporated into the housing body e.g. by twin-shot molding. The windows 11a, 11b may be molded during a first shot in a translucent (and preferably transparent) material, and the outer cover of the housing is molded during a second shot in an opaque material.

In the embodiment of FIGS. 1 to 3b the housing comprises an insert 12 as an integral part located as an inner wall near the distal end of the housing. The insert 12 may be molded in the translucent material. As an alternative, the insert or parts thereof may be formed in the opaque material or as a separate component part as depicted in the embodiment of FIG. 4.

The insert 12 is a cup-shaped component part with a sidewall 13 and a tube 14 extending through the insert 12, thus forming an annular space there between. Arms 15 extend radially outwards from the sidewall 13. A bottom wall 16 connects the sidewall 13 and the tube 14 on the distal side of the insert 12, whereas the opposite proximal side is open. The insert 12 has various interfaces. For example, the tube 14 of insert 12 comprises an inner thread 17 engaging the piston rod 30. In addition, the radial space between the tube 14 and the outer sidewall 13 may provide a bearing area receiving the drive spring 90 and the clutch spring 130. Further, spline teeth 18 are provided on the insert 12 engaging corresponding spline teeth 41 at the distal end of drive sleeve 40. Teeth 18 interact with drive sleeve 40 to rotationally couple and de-couple the drive sleeve and the housing 10.

Figure 4:
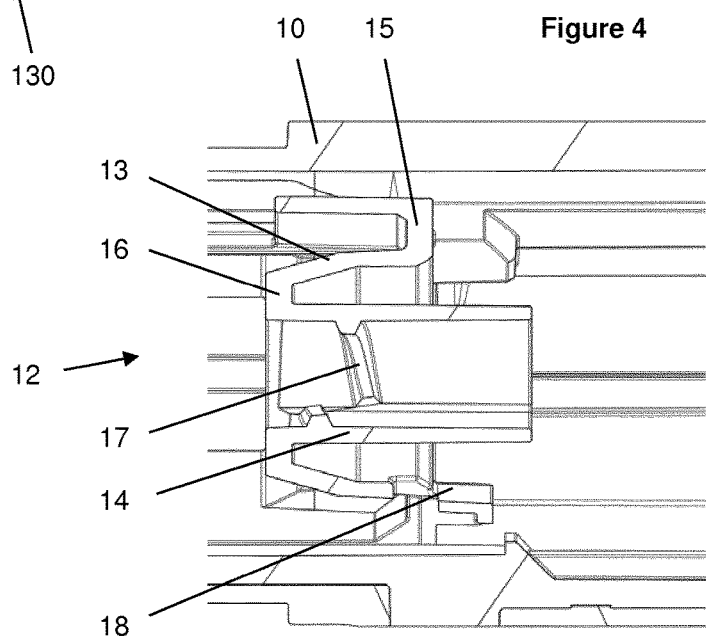
FIG. 4 shows in a sectional view a detail of a device according to a second embodiment.

In the embodiment of FIG. 4, the insert is an integral part of an inner housing shell which inner shell is partially surrounded by an external housing shell. The shells may be formed by two consecutive shots of injection molding such that the shells are permanently attached to each other. For example, the inner shell is formed from a transparent or translucent material, whereas the outer shell is formed from an opaque material.

Figure 5A:
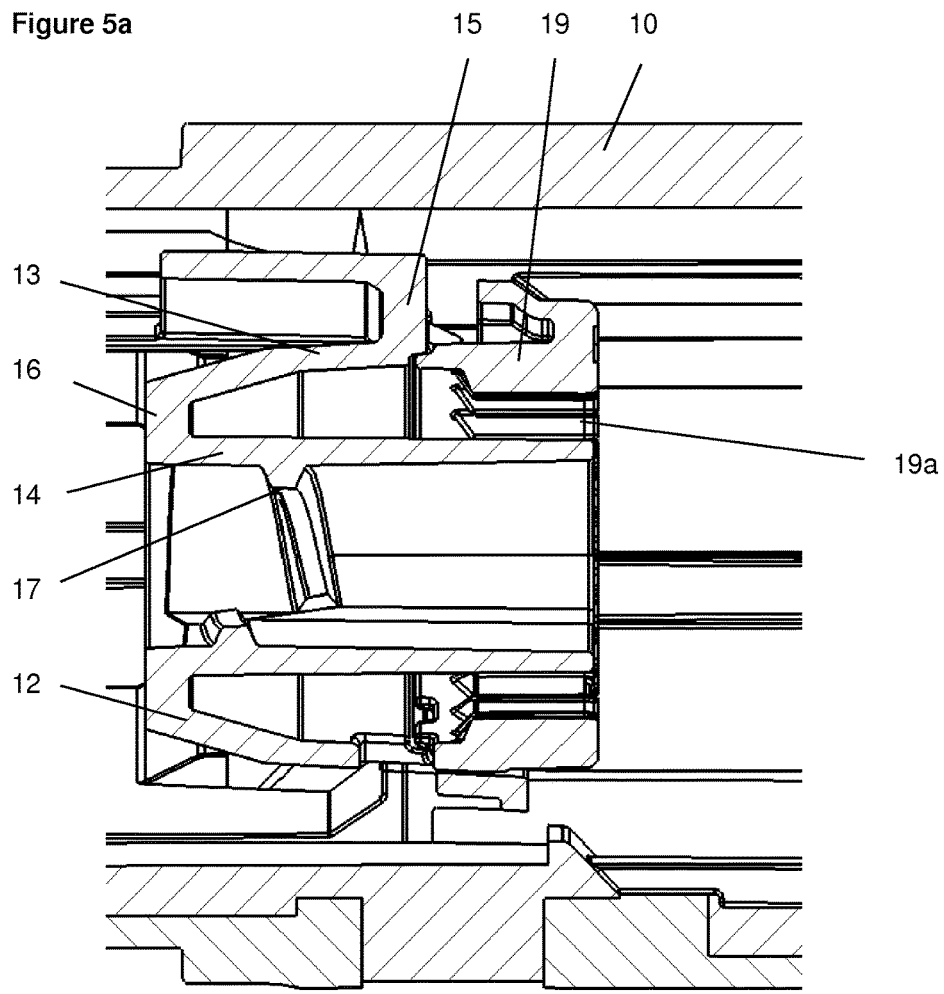
FIG. 5a shows in a sectional view a detail of a device according to a third embodiment.
Figure 5B:
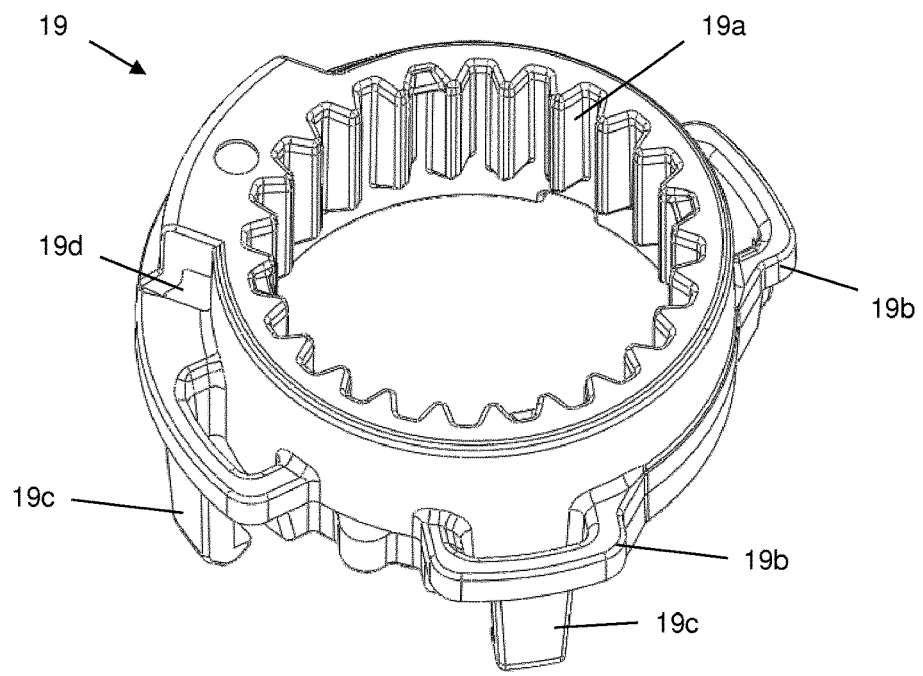

In the embodiment of FIGS. 5a and 5b, the insert 12 is partially formed as one single component part with the housing 10 and partially as a separate component part 19. The cup-shaped body 13 and the threaded tube 14 with the annular space for a compression spring are integrally formed with the housing 10 and connected thereto via arms 15, whereas the clutch feature 18 for rotationally constraining the drive sleeve 40 is a separate ring-shaped component part 19 which is axially and rotationally constrained to the housing 10. Thus, according to the embodiment of FIGS. 5a and 5b, the ring-shaped insert part 19 does not have the thread 17 as an integral part. As shown in FIG. 5b in more detail, the ring-shaped insert part 19 comprises axially orientated splines 19a on an inner surface to rotationally restrain the drive sleeve 40. The ring-shaped insert part 19 further comprises arms or splines 19b on its outer surface for rotational retention within the housing 10. Further, several hook-like arms 19c are provided to form a snap clip for axial retention of the ring-shaped insert part 19 within the housing 10. The ring-shaped insert part 19 comprises a hole or pocket 19d for receiving and fixing the hook end 91 of the drive spring 90. In addition, there are features on the ring-shaped insert part 19 that bias the insert parts 12, 19 axially and rotationally to remove free play.

The cartridge holder 20 is located at the distal side of housing 10 and permanently attached thereto. The cartridge holder may be a transparent or translucent component which is tubular to receive cartridge 100. The distal end of cartridge holder 20 may be provided with means for attaching a needle arrangement. A removable cap (not shown) may be provided to fit over the cartridge holder 20 and may be retained via clip features on the housing 10.

The piston rod 30 is rotationally constrained to the drive sleeve 40 via a splined interface. When rotated, the piston rod 30 is forced to move axially relative to the drive sleeve 40, through its threaded interface with the insert 12 of housing 10. The lead screw 30 is an elongate member with an outer thread engaging the corresponding thread of the insert 12 of housing 10. The interface comprises at least one longitudinal groove or track and a corresponding protrusion or spline of the driver 40. At its distal end, the lead screw 30 is provided with an interface for clip attachment of the bearing 140.

The drive sleeve 40 is a hollow member surrounding the lead screw 30 and arranged within number sleeve 60. It extends from an interface with the clutch plate 120 to the contact with the clutch spring 130. The drive sleeve 40 is axially movable relative to the housing 10, the piston rod 30 and the number sleeve 60 in the distal direction against the bias of clutch spring 130 and in the opposite proximal direction under the bias of clutch spring 130.

Figure 3A:
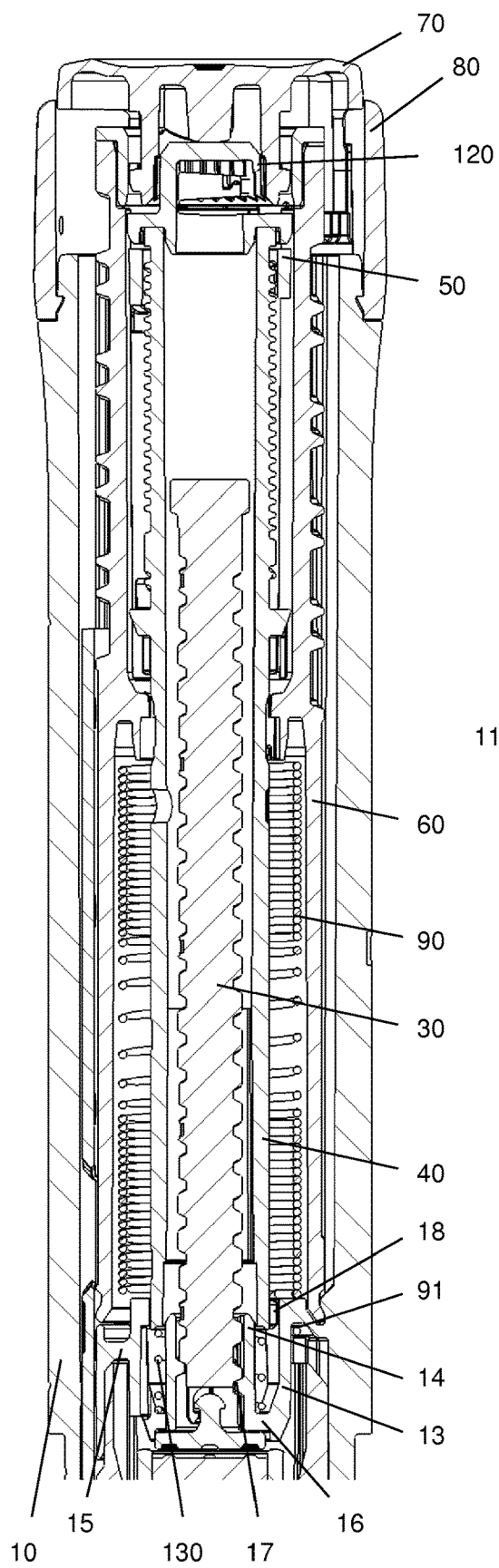
FIG. 3a shows a sectional view of the proximal end of the device of FIG. 1 in a dose setting state.

A splined tooth interface 18 with the insert 12 prevents rotation of the drive sleeve 40 during dose setting. This interface comprises a ring of radially extending outer teeth 41 at the distal end of drive sleeve 40 and corresponding radially extending inner teeth 18 of the housing component 10 (insert 12). When the button 70 is pressed (FIG. 3*b*), these drive sleeve to housing insert spline teeth are disengaged allowing the drive sleeve 40 to rotate relative to the insert and, thus, to housing 10. The clutch spring 130 biases the drive sleeve 40 into a position engaging the teeth of the clutch spring 41 with the teeth 18 of the insert (FIG. 3*a*). A further splined tooth interface with the number sleeve 60 is not engaged during dialing, but engages when the button 70 is pressed, preventing relative rotation between the drive sleeve 40 and number sleeve 60 during dispense. In a preferred embodiment this interface comprises inwardly directed splines on a flange on the inner surface of the number sleeve 60 and a ring of radially extending outer splines of drive sleeve 40. These corresponding splines are located on the number sleeve 60 and the drive sleeve 40, respectively, such that axial movement of the drive sleeve 40 relative to the (axially fixed) number sleeve 60 engages or disengages the splines to rotationally couple or decouple the drive sleeve 40 and the number sleeve 60.

A further interface of the drive sleeve 40 comprises a ring of ratchet teeth located at the proximal end face of drive sleeve 40 and a ring of corresponding ratchet teeth on the clutch plate 120.

The driver 40 has a threaded section providing a helical track for the nut 50. In addition, a last dose abutment or stop is provided which may be the end of the thread track or preferably a rotational hard stop for interaction with a corresponding last dose stop of nut 50, thus limiting movement of the nut 50 on the driver thread. At least one longitudinal spline of the driver 40 engages a corresponding track of the lead screw 30.

The last dose nut 50 is located between the number sleeve 60 and the drive sleeve 40. It is rotationally constrained to the number sleeve 60, via a splined interface. It moves along a helical path relative to the drive sleeve 40, via a threaded interface, when relative rotation occurs between the number sleeve 60 and drive sleeve 40 which is during dialing only. As an alternative, the nut 50 may be splined to the driver 40 and threaded to the number sleeve 60. A last dose stop is provided on nut 50 engaging a stop of drive sleeve 40 when a dose is set corresponding to the remaining dispensable amount of medicament in the cartridge 100.

The dose indicator or number sleeve 60 is a tubular element. The number sleeve 60 is rotated during dose setting (via dose selector 80) and dose correction and during dose dispensing by a torsion spring 90. Together with gauge element 110 the number sleeve 60 defines a zero position ('at rest') and a maximum dose position. Thus, the number sleeve 60 may be seen as a dose setting member.

For manufacturing reasons, the number sleeve 60 of the embodiment shown in the Figures comprises a number sleeve lower 60*a* which is rigidly fixed to a number sleeve upper 60*b* during assembly to form the number sleeve 60. Number sleeve lower 60*a* and number sleeve upper 60*b* are separate components only to simplify number sleeve 60 mold tooling and assembly. As an alternative, the number sleeve 60 may be a unitary component. The number sleeve 60 is constrained to the housing 10 by snap engagement to allow rotation but not translation. The number sleeve 60 comprises an annular recess or groove near its distal end which engages a corresponding bead on an inner surface of the housing 10. The number sleeve lower 60*a* is marked with a sequence of numbers, which are visible through the gauge element 110 and the openings 11*a*, 11*b* in the housing 10, to denote the dialed dose of medicament.

Further, the number sleeve lower 60*a* has a portion with an outer thread engaging the gauge element 110. End stops are provided at the opposite ends of thread to limit relative movement with respect to the gauge element 110.

Clutch features which have the form of a ring of splines are provided inwardly directed on number sleeve upper 60*b* for engagement with splines of the button 70 during dose setting and dose correction. A clicker arm is provided on the outer surface of number sleeve 60 which interacts with the drive sleeve 40 and the gauge member 110 for generating a feedback signal. In addition, the number sleeve lower 60*a* is rotationally constrained to the nut 50 and to the clutch plate 120 via a splined interface comprising at least one longitudinal spline. Further, number sleeve lower 60*a* comprises an interface for attachment of the torsion spring 90.

The button 70 which forms the proximal end of the device is permanently splined to the dose selector 80. A central stem extends distally from the proximal actuation face of the button 70. The stem is provided with a flange carrying the splines for engagement with splines of the number sleeve upper 60*b*. Thus, it is also splined via splines to the number sleeve upper 60*b* when the button 70 is not pressed, but this spline interface is disconnected when the button 70 is pressed. The button 70 has a discontinuous annular skirt with splines. When the button 70 is pressed, splines on the button 70 engage with splines on the housing 10, preventing rotation of the button 70 (and hence the dose selector 80) during dispense. These splines disengage when the button 70 is released, allowing a dose to be dialed. Further, a ring of ratchet teeth is provided on the inner side of button flange for interaction with clutch plate 120.

The dose selector 80 is axially constrained to the housing 10. It is rotationally constrained, via the splined interface, to the button 70. This splined interface which includes grooves interacting with spline features formed by the annular skirt of button 70 remains engaged irrespective of the dose button 70 axial positions. The dose selector 80 or dose dial grip is a sleeve-like component with a serrated outer skirt.

The torsion spring 90 is attached at its distal end by a hook 91 to the insert 12 and, thus, to the housing 10 and at the other end to the number sleeve 60. The torsion spring 90 is located inside the number sleeve 60 and surrounds a distal portion of the drive sleeve 40. The torsion spring 90 is pre-wound upon assembly, such that it applies a torque to the number sleeve 60 when the mechanism is at dialed zero units. The action of rotating the dose selector 80, to set a dose, rotates the number sleeve 60 relative to the housing 10, and charges the torsion spring 90 further.

The cartridge 100 is received in cartridge holder 20. The cartridge 100 may be a glass ampoule having a moveable rubber bung at its proximal end. The distal end of cartridge 100 is provided with a pierceable rubber seal which is held in place by a crimped annular metal band. In the embodiment depicted in the Figures, the cartridge 100 is a standard 1.5 ml cartridge. The device is designed to be disposable in that the cartridge 100 cannot be replaced by the user or health care professional. However, a reusable variant of the device could be provided by making the cartridge holder 20 removable and allowing backwinding of the lead screw 30 and the resetting of nut 50.

The gauge element 110 is constrained to prevent rotation but allow translation relative to the housing 10 via a splined interface. The gauge element 110 has a helical feature on its inner surface which engages with the helical thread cut in the number sleeve 60 such that rotation of the number sleeve 60 causes axial translation of the gauge element 110. This helical feature on the gauge element 110 also creates stop abutments against the end of the helical cut in the number sleeve 60 to limit the minimum and maximum dose that can be set.

The gauge element 110 has a generally plate or band like component having a central aperture or window and two flanges extending on either side of the aperture. The flanges are preferably not transparent and thus shield or cover the number sleeve 60, whereas the aperture or window allows viewing a portion of the number sleeve lower 60a. Further, gauge element 110 has a cam and a recess interacting with the clicker arm of the number sleeve 60 at the end of dose dispensing.

The clutch plate 120 is a ring-like component. The clutch plate 120 is splined to the number sleeve 60 via splines. It is also coupled to the drive sleeve 40 via a ratchet interface. The ratchet provides a detented position between the number sleeve 60 and drive sleeve 40 corresponding to each dose unit, and engages different ramped tooth angles during clockwise and anti-clockwise relative rotation. A clicker arm is provided on the clutch plate 120 for interaction with ratchet features of the button 70.

The clutch spring 130 is a compression spring. The axial position of the drive sleeve 40, clutch plate 120 and button 70 is defined by the action of the clutch spring 130, which applies a force on the drive sleeve 40 in the proximal direction. This spring force is reacted via the drive sleeve 40, clutch plate 120, and button 70, and when 'at rest' it is further reacted through the dose selector 80 to the housing 10. The spring force ensures that the ratchet interface between drive sleeve 40 and clutch plate 120 is always engaged. In the 'at rest' position, it also ensures that the button splines are engaged with the number sleeve splines, and the drive sleeve teeth are engaged with teeth of the housing 10.

The bearing 140 is axially constrained to the piston rod 30 and acts on the bung within the liquid medicament cartridge. It is axially clipped to the lead screw 30, but free to rotate.

With the device in the 'at rest' condition as shown in FIGS. 1 and 3a, the number sleeve 60 is positioned against its zero dose abutment with the gauge element 110 and the button 70 is not depressed. Dose marking '0' on the number sleeve 60 is visible through the window 11b of the housing 10 and gauge element 110, respectively.

The torsion spring 90, which has a number of pre-wound turns applied to it during assembly of the device, applies a torque to the number sleeve 60 and is prevented from rotating by the zero dose abutment.

The user selects a variable dose of liquid medicament by rotating the dose selector 80 clockwise, which generates an identical rotation in the number sleeve 60. Rotation of the number sleeve 60 causes charging of the torsion spring 90, increasing the energy stored within it. As the number sleeve 60 rotates, the gauge element 110 translates axially due to its threaded engagement thereby showing the value of the dialed dose. The gauge element 110 has flanges either side of the window area which cover the numbers printed on the number sleeve 60 adjacent to the dialed dose to ensure only the set dose number is made visible to the user.

A feature of some embodiments is the inclusion of a visual feedback feature in addition to the discrete dose number display typical on devices of this type. The distal end of the gauge element 110 creates a sliding scale through the small window 11a in the housing 10. As an alternative, the sliding scale could be formed using a separate component engaged with the number sleeve 60 on a different helical track.

As a dose is set by the user, the gauge element 110 translates axially, the distance moved proportional to the magnitude of the dose set. This feature gives clear feedback to the user regarding the approximate size of the dose set. The dispense speed of an auto-injector mechanism may be higher than for a manual injector device, so it may not be possible to read the numerical dose display during dispense. The gauge feature provides feedback to the user during dispense regarding dispense progress without the need to read the dose number itself. For example, the gauge display may be formed by an opaque element on the gauge element 110 revealing a contrasting colored component underneath. Alternatively, the revealable element may be printed with coarse dose numbers or other indices to provide more precise resolution. In addition, the gauge display simulates a syringe action during dose setting and dispensing.

The drive sleeve 40 is prevented from rotating as the dose is set and the number sleeve 60 rotated, due to the engagement of its splined teeth with teeth of the housing 10. Relative rotation must therefore occur between the clutch plate 120 and drive sleeve 40 via the ratchet interface.

The user torque required to rotate the dose selector 80 is a sum of the torque required to wind up the torsion spring 90, and the torque required to overhaul the ratchet interface. The clutch spring 130 is designed to provide an axial force to the ratchet interface and to bias the clutch plate 120 onto the drive sleeve 40. This axial load acts to maintain the ratchet teeth engagement of the clutch plate 120 and drive sleeve 40. The torque required to overhaul the ratchet in the dose set direction is a function of the axial load applied by the clutch spring 130, the clockwise ramp angle of the ratchet teeth, the friction coefficient between the mating surfaces and the mean radius of the ratchet interface.

As the user rotates the dose selector 80 sufficiently to increment the mechanism by one increment, the number sleeve 60 rotates relative to the drive sleeve 40 by one ratchet tooth. At this point the ratchet teeth re-engage into the next detented position. An audible click is generated by the ratchet re-engagement, and tactile feedback is given by the change in torque input required.

Relative rotation of the number sleeve 60 and the drive sleeve 40 is allowed. This relative rotation also causes the last dose nut 50 to travel along its threaded path, towards its last dose abutment on the drive sleeve 40.

With no user torque applied to the dose selector 80, the number sleeve 60 is now prevented from rotating back under the torque applied by the torsion spring 90, solely by the ratchet interface between the clutch plate 120 and the drive sleeve 40. The torque necessary to overhaul the ratchet in the anti-clockwise direction is a function of the axial load applied by the clutch spring 130, the anti-clockwise ramp angle of the ratchet, the friction coefficient between the mating surfaces and the mean radius of the ratchet features. The torque necessary to overhaul the ratchet must be greater than the torque applied to the number sleeve 60 (and hence clutch plate 120) by the torsion spring 90. The ratchet ramp angle is therefore increased in the anti-clockwise direction to ensure this is the case whilst ensuring the dial-up torque is as low as possible.

The user may now choose to increase the selected dose by continuing to rotate the dose selector 80 in the clockwise direction. The process of overhauling the ratchet interface between the number sleeve 60 and drive sleeve 40 is repeated for each dose increment. Additional energy is stored within the torsion spring 90 for each dose increment and audible and tactile feedback is provided for each increment dialed by the re-engagement of the ratchet teeth. The torque required to rotate the dose selector 80 increases as the torque required to wind up the torsion spring 90 increases. The torque required to overhaul the ratchet in the anti-clockwise direction must therefore be greater than the torque applied to the number sleeve 60 by the torsion spring 90 when the maximum dose has been reached.

If the user continues to increase the selected dose until the maximum dose limit is reached, the number sleeve 60 engages with its maximum dose abutment on the maximum dose abutment of gauge element 110. This prevents further rotation of the number sleeve 60, clutch plate 120 and dose selector 80.

Depending on how many increments have already been delivered by the mechanism, during selection of a dose, the last dose nut 50 may contact its last dose abutment with stop face of the drive sleeve 40. The abutment prevents further relative rotation between the number sleeve 60 and the drive sleeve 40, and therefore limits the dose that can be selected. The position of the last dose nut 50 is determined by the total number of relative rotations between the number sleeve 60 and drive sleeve 40, which have occurred each time the user sets a dose.

With the mechanism in a state in which a dose has been selected, the user is able to deselect any number of increments from this dose. Deselecting a dose is achieved by the user rotating the dose selector 80 anti-clockwise. The torque applied to the dose selector 80 by the user is sufficient, when combined with the torque applied by the torsion spring 90, to overhaul the ratchet interface between the clutch plate 120 and drive sleeve 40 in the anti-clockwise direction. When the ratchet is overhauled, anti-clockwise rotation occurs in the number sleeve 60 (via the clutch plate 120), which returns the number sleeve 60 towards the zero dose position, and unwinds the torsion spring 90. The relative rotation between the number sleeve 60 and drive sleeve 40 causes the last dose nut 50 to return along its helical path, away from the last dose abutment.

Figure 3B:
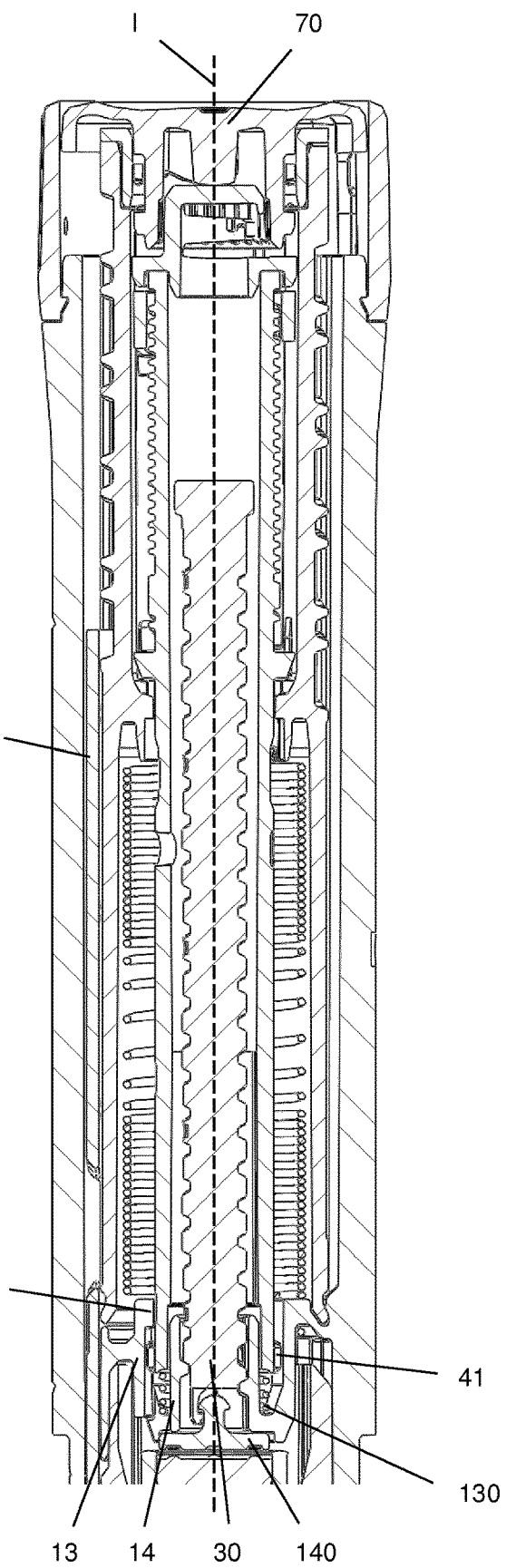
FIG. 3b shows a sectional view of the proximal end of the device of FIG. 1 in a dose dispensing state.

With the mechanism in a state in which a dose has been selected, the user is able to activate the mechanism to commence delivery of a dose. Delivery of a dose is initiated by the user depressing the button 70 axially in the distal direction (FIG. 3b).

When the button 70 is depressed, splines between the button 70 and number sleeve 60 are disengaged, rotationally disconnecting the button 70 and dose selector 80 from the delivery mechanism, i.e. from number sleeve 60, gauge element 110 and torsion spring 90. Splines on the button 70 engage with splines on the housing 10, preventing rotation of the button 70 (and hence the dose selector 80) during dispense. As the button 70 is stationary during dispense, it can be used in the dispense clicker mechanism. A stop feature in the housing 10 limits axial travel of the button 70 and reacts to any axial abuse loads applied by the user, reducing the risk of damaging internal components.

The clutch plate 120 and drive sleeve 40 travel axially with the button 70. This engages the splined tooth interface between the drive sleeve 40 and number sleeve 60, preventing relative rotation between the drive sleeve 40 and number sleeve 60 during dispense. The splined tooth interface 18, 41 between the drive sleeve 40 and the housing insert 12 disengages, so the drive sleeve 40 can now rotate and is driven by the torsion spring 90 via the number sleeve 60, and clutch plate 120.

Rotation of the drive sleeve 40 causes the piston rod 30 to rotate due to their splined engagement, and the piston rod 30 then advances due to its threaded engagement to the housing 10. The number sleeve 60 rotation also causes the gauge element 110 to traverse axially back to its zero position whereby the zero dose abutment stops the mechanism.

Tactile feedback during dose dispense is provided via the compliant cantilever clicker arm integrated into the clutch plate 120. This arm interfaces radially with ratchet features on the inner surface of the button 70, whereby the ratchet tooth spacing corresponds to the number sleeve 60 rotation required for a single increment dispense. During dispense, as the number sleeve 60 rotates and the button 70 is rotationally coupled to the housing 10, the ratchet features engage with the clicker arm to produce an audible click with each dose increment delivered.

Delivery of a dose continues via the mechanical interactions described above while the user continues to depress the button 70. If the user releases the button 70, the clutch spring 130 returns the drive sleeve 40 to its 'at rest' position (together with the clutch plate 120 and button 70), engaging the splines between the drive sleeve 40 and housing 10, preventing further rotation and stopping dose delivery.

During delivery of a dose, the drive sleeve 40 and number sleeve 60 rotate together, so that no relative motion in the last dose nut 50 occurs. The last dose nut 50 therefore travels axially relative to the drive sleeve 40 during dialing only.

Once the delivery of a dose is stopped, by the number sleeve 60 returning to the zero dose abutment, the user may release the button 70, which will re-engage the spline teeth between the drive sleeve 40 and housing 10. The mechanism is now returned to the 'at rest' condition.

At the end of dose dispensing, additional audible feedback is provided in the form of a 'click', distinct from the 'clicks' provided during dispense, to inform the user that the device has returned to its zero position via the interaction of the clicker arm on the number sleeve 60 with the ramp on the drive sleeve 40 and the cam and the recess on the gauge element 110. This embodiment allows feedback to only be created at the end of dose delivery and not created if the device is dialed back to, or away from, the zero position.

| Reference Numerals: | |
| --- | --- |
| 10 | housing (casing) |
| 11a, b | window |
| 12 | insert |
| 13 | sidewall |
| 14 | tube |
| 15 | arm |
| 16 | bottom wall |
| 17 | thread |
| 18 | spline teeth |
| 19 | ring-shaped second part |
| 19a | spline teeth |
| 19b | arm (spline) |
| 19c | arm (snap clip) |
| 19d | opening |
| 20 | cartridge holder |
| 30 | piston rod (lead screw) |
| 40 | drive sleeve |
| 41 | spline teeth |
| 50 | nut |
| 60 | dose setting element |
| 60a | number sleeve lower |
| 60b | number sleeve upper |
| 70 | button |
| 80 | dose selector |
| 90 | torsion spring |
| 91 | hook |

| Reference Numerals: | |
|---|---|
| 100 | cartridge |
| 110 | gauge element |
| 120 | clutch plate |
| 130 | clutch spring |
| 140 | bearing |
| I | axis |

The invention claimed is:

1. A drug delivery device for selecting and dispensing a number of user variable doses of a medicament, the drug delivery device comprising:
   a housing,
   a cartridge holder,
   a cartridge containing a medicament,
   a piston rod,
   a drive member,
   a compression spring, and
   an insert comprising:
      a first part having a cup-shaped body with a distal end and a proximal end, the body having a sidewall,
      a tube extending centrally through the cup-shaped body in a longitudinal direction defining an annular space between the sidewall and the tube, wherein the annular space is open in the proximal end direction for receiving the compression spring, wherein the tube comprises a thread for engaging an outer thread of the piston rod, the thread being provided at an inner surface of the tube, and wherein at least one of the tube, the sidewall, and a separate second part of the insert comprises a first clutch feature for rotationally constraining the drive member to the insert, and
      at least one arm extending radially outwards from the sidewall, wherein the at least one arm is configured to lock the first part of the insert to the housing for rotationally and axially constraining the insert to the housing, or the first part of the insert is integrally connected to the housing by the at least one arm to form one single component part with the housing.

2. The drug delivery device according to claim 1, wherein the annular space between the sidewall and the tube defines a portion for receiving or guiding the drive member, the drive member being axially displaceable.

3. The drug delivery device according to claim 1, wherein the cup-shaped body comprises a radially extending bottom wall closing the annular space at the distal end.

4. The drug delivery device according to claim 1, wherein the first part is integrally formed with the housing of the drug delivery device and wherein the separate second part is axially or rotationally constrained to the first part or the housing of the drug delivery device.

5. The drug delivery device according to claim 4, wherein the first part comprises the sidewall and the tube with the thread, and wherein the second part comprises the first clutch feature.

6. The drug delivery device according to claim 4, further comprising a drive spring, wherein a proximal end of the sidewall, the at least one arm or the second part comprises an opening that receives a hook end of the drive spring.

7. The drug delivery device according to claim 1, further comprising at least one member selected from the group consisting of:

a nut,
a dose setting element,
a button,
a dose setting grip,
a gauge element, and
a clutch plate.

8. The drug delivery device according to claim 1, wherein the piston rod has an outer diameter equal to or smaller than an inner diameter of the tube of the insert.

9. The drug delivery device according to claim 1, wherein the drive member is an axially displaceable tubular element at least partly surrounding the piston rod, wherein a distal end of the drive member has an inner diameter equal to or larger than an outer diameter of the tube of the insert and the drive member has an outer diameter equal to or smaller than an inner diameter of the sidewall of the insert.

10. The drug delivery device according to claim 1, wherein the drive member comprises axially extending splines provided at an outer surface of the drive member, and wherein the first clutch feature for rotationally constraining the drive member to the insert comprises axially extending splines provided at an inner surface of the sidewall of the insert or on the second part.

11. The drug delivery device according to claim 1, wherein the compression spring located within the annular space interposed between the insert and a drive member is a clutch spring.

12. The drug delivery device according to claim 1, wherein the drive spring is in the form of a torsion spring having at least one hook configured to engage an opening of the insert, the at least one hook being at a distal end of the torsion spring.

13. The drug delivery device according to claim 4, further comprising a drive spring, wherein a proximal end of the sidewall, the at least one arm and the second part, and the second part defines an opening that receives a hook end of the drive spring.

* * * * *

SEQUENCE LISTING

<160> NUMBER OF SEQ ID NOS: 40

<210> SEQ ID NO 1
<211> LENGTH: 39
<212> TYPE: PRT
<213> ORGANISM: Artificial Sequence
<220> FEATURE:
<223> OTHER INFORMATION: Exendin-4

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 41
<212> TYPE: PRT
<213> ORGANISM: Artificial Sequence
<220> FEATURE:
<223> OTHER INFORMATION: H-(Lys)4-des Pro36, des Pro37 Exendin-4(1-39)-
    NH2

<400> SEQUENCE: 2

Lys Lys Lys Lys His Gly Glu Gly Thr Phe Thr Ser Asp Leu Ser Lys
1               5                   10                  15

Gln Met Glu Glu Glu Ala Val Arg Leu Phe Ile Glu Trp Leu Lys Asn
            20                  25                  30

Gly Gly Pro Ser Ser Gly Ala Pro Ser
        35                  40

<210> SEQ ID NO 3
<211> LENGTH: 42
<212> TYPE: PRT
<213> ORGANISM: Artificial Sequence
<220> FEATURE:
<223> OTHER INFORMATION: H-(Lys)5-des Pro36, des Pro37 Exendin-4(1-39)-
    NH2

<400> SEQUENCE: 3

Lys Lys Lys Lys Lys His Gly Glu Gly Thr Phe Thr Ser Asp Leu Ser
1               5                   10                  15

Lys Gln Met Glu Glu Glu Ala Val Arg Leu Phe Ile Glu Trp Leu Lys
            20                  25                  30

Asn Gly Gly Pro Ser Ser Gly Ala Pro Ser
        35                  40

<210> SEQ ID NO 4
<211> LENGTH: 38
<212> TYPE: PRT
<213> ORGANISM: Artificial Sequence
<220> FEATURE:
<223> OTHER INFORMATION: des Pro36 Exendin-4(1-39)

```
<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 5
<211> LENGTH: 38
<212> TYPE: PRT
<213> ORGANISM: Artificial Sequence
<220> FEATURE:
<223> OTHER INFORMATION: des Pro36 [Asp28] Exendin-4(1-39)

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 6
<211> LENGTH: 39
<212> TYPE: PRT
<213> ORGANISM: Artificial Sequence
<220> FEATURE:
<223> OTHER INFORMATION: des Pro36 [IsoAsp28] Exendin-4(1-39)
<220> FEATURE:
<221> NAME/KEY: MISC_FEATURE
<222> LOCATION: (28)..(28)
<223> OTHER INFORMATION: X = isoaspartate

<400> SEQUENCE: 6

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Xaa Gly Gly Pro Ser
            20                  25                  30

Ser Gly Ala Pro Pro Pro Ser
        35

<210> SEQ ID NO 7
<211> LENGTH: 38
<212> TYPE: PRT
<213> ORGANISM: Artificial Sequence
<220> FEATURE:
<223> OTHER INFORMATION: des Pro36 [Met(O)14, Asp28] Exendin-4(1-39)
<220> FEATURE:
<221> NAME/KEY: MISC_FEATURE
<222> LOCATION: (14)..(14)
<223> OTHER INFORMATION: X = methionine oxide

<400> SEQUENCE: 7

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 8
```

```
<211> LENGTH: 38
<212> TYPE: PRT
<213> ORGANISM: Artificial Sequence
<220> FEATURE:
<223> OTHER INFORMATION: des Pro36 [Met(O)14, IsoAsp28] Exendin-4(1-39)
<220> FEATURE:
<221> NAME/KEY: MISC_FEATURE
<222> LOCATION: (14)..(14)
<223> OTHER INFORMATION: X = methionine oxide
<220> FEATURE:
<221> NAME/KEY: MISC_FEATURE
<222> LOCATION: (28)..(28)
<223> OTHER INFORMATION: X = isoaspartate

<400> SEQUENCE: 8

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Xaa Gly Gly Pro Ser
            20                  25                  30

Ser Gly Ala Pro Pro Ser
        35

<210> SEQ ID NO 9
<211> LENGTH: 38
<212> TYPE: PRT
<213> ORGANISM: Artificial Sequence
<220> FEATURE:
<223> OTHER INFORMATION: des Pro36 [Trp(O2)25, Asp28] Exendin-4(1-39)
<220> FEATURE:
<221> NAME/KEY: MISC_FEATURE
<222> LOCATION: (25)..(25)
<223> OTHER INFORMATION: X = tryptophan dioxide

<400> SEQUENCE: 9

His Gly Glu Gly Thr Phe Thr Ser Asp Leu Ser Lys Gln Met Glu Glu
1               5                   10                  15

Glu Ala Val Arg Leu Phe Ile Glu Xaa Leu Lys Asp Gly Gly Pro Ser
            20                  25                  30

Ser Gly Ala Pro Pro Ser
        35

<210> SEQ ID NO 10
<211> LENGTH: 38
<212> TYPE: PRT
<213> ORGANISM: Artificial Sequence
<220> FEATURE:
<223> OTHER INFORMATION: des Pro36 [Trp(O2)25, IsoAsp28] Exendin-4(1-39)
<220> FEATURE:
<221> NAME/KEY: MISC_FEATURE
<222> LOCATION: (25)..(25)
<223> OTHER INFORMATION: X = tryptophan dioxide
<220> FEATURE:
<221> NAME/KEY: MISC_FEATURE
<222> LOCATION: (28)..(28)
<223> OTHER INFORMATION: X = isoaspartate

<400> SEQUENCE: 10

His Gly Glu Gly Thr Phe Thr Ser Asp Leu Ser Lys Gln Met Glu Glu
1               5                   10                  15

Glu Ala Val Arg Leu Phe Ile Glu Xaa Leu Lys Xaa Gly Gly Pro Ser
            20                  25                  30

Ser Gly Ala Pro Pro Ser
        35

<210> SEQ ID NO 11
<211> LENGTH: 38
<212> TYPE: PRT
```

```
<213> ORGANISM: Artificial Sequence
<220> FEATURE:
<223> OTHER INFORMATION: des Pro36 [Met(O)14 Trp(O2)25, Asp28]
      Exendin-4(1-39)
<220> FEATURE:
<221> NAME/KEY: MISC_FEATURE
<222> LOCATION: (14)..(14)
<223> OTHER INFORMATION: X = methionine oxide
<220> FEATURE:
<221> NAME/KEY: MISC_FEATURE
<222> LOCATION: (25)..(25)
<223> OTHER INFORMATION: X = tryptophan dioxide

<400> SEQUENCE: 11

His Gly Glu Gly Thr Phe Thr Ser Asp Leu Ser Lys Gln Xaa Glu Glu
1               5                   10                  15

Glu Ala Val Arg Leu Phe Ile Glu Xaa Leu Lys Asp Gly Gly Pro Ser
            20                  25                  30

Ser Gly Ala Pro Pro Ser
        35

<210> SEQ ID NO 12
<211> LENGTH: 38
<212> TYPE: PRT
<213> ORGANISM: Artificial Sequence
<220> FEATURE:
<223> OTHER INFORMATION: des Pro36 [Met(O)14 Trp(O2)25, IsoAsp28]
      Exendin-4(1-39)
<220> FEATURE:
<221> NAME/KEY: MISC_FEATURE
<222> LOCATION: (14)..(14)
<223> OTHER INFORMATION: X = methionine oxide
<220> FEATURE:
<221> NAME/KEY: MISC_FEATURE
<222> LOCATION: (25)..(25)
<223> OTHER INFORMATION: X = tryptophan dioxide
<220> FEATURE:
<221> NAME/KEY: MISC_FEATURE
<222> LOCATION: (28)..(28)
<223> OTHER INFORMATION: X = isoapartate

<400> SEQUENCE: 12

His Gly Glu Gly Thr Phe Thr Ser Asp Leu Ser Lys Gln Xaa Glu Glu
1               5                   10                  15

Glu Ala Val Arg Leu Phe Ile Glu Xaa Leu Lys Xaa Gly Gly Pro Ser
            20                  25                  30

Ser Gly Ala Pro Pro Ser
        35

<210> SEQ ID NO 13
<211> LENGTH: 44
<212> TYPE: PRT
<213> ORGANISM: Artificial Sequence
<220> FEATURE:
<223> OTHER INFORMATION: des Pro36 Exendin-4(1-39)-Lys6-NH2

<400> SEQUENCE: 13

His Gly Glu Gly Thr Lys Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 14
<211> LENGTH: 50
<212> TYPE: PRT
```

<213> ORGANISM: Artificial Sequence
<220> FEATURE:
<223> OTHER INFORMATION: H-(Lys)6-des Pro36 [Asp28] Exendin-4(1-39)-
     Lys6-NH2

<400> SEQUENCE: 14

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 15
<211> LENGTH: 38
<212> TYPE: PRT
<213> ORGANISM: Artificial Sequence
<220> FEATURE:
<223> OTHER INFORMATION: des Asp28 Pro36, Pro37, Pro38Exendin-4(1-39)-
     NH2

<400> SEQUENCE: 15

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gly Gly Pro Ser Ser
            20                  25                  30

Gly Ala Pro Pro Pro Ser
        35

<210> SEQ ID NO 16
<211> LENGTH: 44
<212> TYPE: PRT
<213> ORGANISM: Artificial Sequence
<220> FEATURE:
<223> OTHER INFORMATION: H-(Lys)6-des Pro36, Pro38 [Asp28]
     Exendin-4(1-39)-NH2

<400> SEQUENCE: 16

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser
        35                  40

<210> SEQ ID NO 17
<211> LENGTH: 44
<212> TYPE: PRT
<213> ORGANISM: Artificial Sequence
<220> FEATURE:
<223> OTHER INFORMATION: H-Asn-(Glu)5des Pro36, Pro37, Pro38 [Asp28]
     Exendin-4(1-39)-NH2

<400> SEQUENCE: 17

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser
        35                  40

<210> SEQ ID NO 18
<211> LENGTH: 44
<212> TYPE: PRT
<213> ORGANISM: Artificial Sequence
<220> FEATURE:
<223> OTHER INFORMATION: des Pro36, Pro37, Pro38 [Asp28]
      Exendin-4(1-39)-(Lys)6-NH2

<400> SEQUENCE: 18

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser Lys Lys Lys Lys Lys Lys
        35                  40

<210> SEQ ID NO 19
<211> LENGTH: 50
<212> TYPE: PRT
<213> ORGANISM: Artificial Sequence
<220> FEATURE:
<223> OTHER INFORMATION: H-(Lys)6-des Pro36, Pro37, Pro38 [Asp28]
      Exendin-4(1-39)-(Lys)6-NH2

<400> SEQUENCE: 19

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 20
<211> LENGTH: 50
<212> TYPE: PRT
<213> ORGANISM: Artificial Sequence
<220> FEATURE:
<223> OTHER INFORMATION: H-Asn-(Glu)5-des Pro36, Pro37, Pro38 [Asp28]
      Exendin-4(1-39)-(Lys)6-NH2

<400> SEQUENCE: 20

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 21
<211> LENGTH: 50
<212> TYPE: PRT
<213> ORGANISM: Artificial Sequence
<220> FEATURE:
<223> OTHER INFORMATION: H-(Lys)6-des Pro36 [Trp(O2)25, Asp28]
      Exendin-4(1-39)-Lys6-NH2
<220> FEATURE:
<221> NAME/KEY: MISC_FEATURE
<222> LOCATION: (31)..(31)
<223> OTHER INFORMATION: X = tryptophan dioxide

<400> SEQUENCE: 21

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Xaa Leu
                20                  25                  30

Lys Asp Gly Gly Pro Ser Ser Gly Ala Pro Pro Ser Lys Lys Lys Lys
            35                  40                  45

Lys Lys
    50

<210> SEQ ID NO 22
<211> LENGTH: 38
<212> TYPE: PRT
<213> ORGANISM: Artificial Sequence
<220> FEATURE:
<223> OTHER INFORMATION: H-des Asp28 Pro36, Pro37, Pro38 [Trp(O2)25]
      Exendin-4(1-39)-NH2
<220> FEATURE:
<221> NAME/KEY: MISC_FEATURE
<222> LOCATION: (25)..(25)
<223> OTHER INFORMATION: X = tryptophan dioxide

<400> SEQUENCE: 22

His Gly Glu Gly Thr Phe Thr Ser Asp Leu Ser Lys Gln Met Glu Glu
1               5                   10                  15

Glu Ala Val Arg Leu Phe Ile Glu Xaa Leu Lys Gly Gly Pro Ser Ser
                20                  25                  30

Gly Ala Pro Pro Pro Ser
        35

<210> SEQ ID NO 23
<211> LENGTH: 44
<212> TYPE: PRT
<213> ORGANISM: Artificial Sequence
<220> FEATURE:
<223> OTHER INFORMATION: H-(Lys)6-des Pro36, Pro37, Pro38 [Trp(O2)25,
      Asp28] Exendin-4(1-39)-NH2
<220> FEATURE:
<221> NAME/KEY: MISC_FEATURE
<222> LOCATION: (31)..(31)
<223> OTHER INFORMATION: X = tryptophan dioxide.

<400> SEQUENCE: 23

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Xaa Leu
                20                  25                  30

Lys Asp Gly Gly Pro Ser Ser Gly Ala Pro Pro Ser
            35                  40

<210> SEQ ID NO 24
<211> LENGTH: 44
<212> TYPE: PRT
<213> ORGANISM: Artificial Sequence
<220> FEATURE:
<223> OTHER INFORMATION: H-Asn-(Glu)5-des Pro36, Pro37, Pro38
      [Trp(O2)25, Asp28] Exendin-4(1-39)-NH2
<220> FEATURE:
<221> NAME/KEY: MISC_FEATURE
<222> LOCATION: (31)..(31)
<223> OTHER INFORMATION: X = tryptophan dioxide

<400> SEQUENCE: 24

Asn Glu Glu Glu Glu Glu His Gly Glu Gly Thr Phe Thr Ser Asp Leu
1               5                   10                  15

```
Ser Lys Gln Met Glu Glu Glu Ala Val Arg Leu Phe Ile Glu Xaa Leu
            20                  25                  30

Lys Asp Gly Gly Pro Ser Ser Gly Ala Pro Pro Ser
            35                  40

<210> SEQ ID NO 25
<211> LENGTH: 44
<212> TYPE: PRT
<213> ORGANISM: Artificial Sequence
<220> FEATURE:
<223> OTHER INFORMATION: des Pro36, Pro37, Pro38 [Trp(O2)25, Asp28]
      Exendin-4(1-39)-(Lys)6-NH2
<220> FEATURE:
<221> NAME/KEY: MISC_FEATURE
<222> LOCATION: (25)..(25)
<223> OTHER INFORMATION: X = tyrptophan dioxide

<400> SEQUENCE: 25

His Gly Glu Gly Thr Phe Thr Ser Asp Leu Ser Lys Gln Met Glu Glu
1               5                   10                  15

Glu Ala Val Arg Leu Phe Ile Glu Xaa Leu Lys Asp Gly Gly Pro Ser
            20                  25                  30

Ser Gly Ala Pro Pro Ser Lys Lys Lys Lys Lys Lys
            35                  40

<210> SEQ ID NO 26
<211> LENGTH: 50
<212> TYPE: PRT
<213> ORGANISM: Artificial Sequence
<220> FEATURE:
<223> OTHER INFORMATION: H-(Lys)6-des Pro36, Pro37, Pro38 [Trp(O2)25,
      Asp28] Exendin-4(1-39)-(Lys)6-NH2
<220> FEATURE:
<221> NAME/KEY: MISC_FEATURE
<222> LOCATION: (31)..(31)
<223> OTHER INFORMATION: X = tryptophan dioxide

<400> SEQUENCE: 26

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
            35                  40                  45

Lys Lys
    50

<210> SEQ ID NO 27
<211> LENGTH: 50
<212> TYPE: PRT
<213> ORGANISM: Artificial Sequence
<220> FEATURE:
<223> OTHER INFORMATION: H-Asn-(Glu)5-des Pro36, Pro37, Pro38
      [Trp(O2)25, Asp28] Exendin-4(1-39)-(Lys)6-NH2
<220> FEATURE:
<221> NAME/KEY: MISC_FEATURE
<222> LOCATION: (31)..(31)
<223> OTHER INFORMATION: X = tryptophan dioxide

<400> SEQUENCE: 27

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Xaa Leu
            20                  25                  30
```

Lys Asp Gly Gly Pro Ser Ser Gly Ala Pro Pro Ser Lys Lys Lys Lys
        35                  40                  45

Lys Lys
    50

<210> SEQ ID NO 28
<211> LENGTH: 50
<212> TYPE: PRT
<213> ORGANISM: Artificial Sequence
<220> FEATURE:
<223> OTHER INFORMATION: H-(Lys)6-des Pro36 [Met(O)14, Asp28]
      Exendin-4(1-39)-Lys6-NH2
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: MISC_FEATURE
<222> LOCATION: (30)..(30)
<223> OTHER INFORMATION: X = methionine oxide

<400> SEQUENCE: 28

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 29
<211> LENGTH: 38
<212> TYPE: PRT
<213> ORGANISM: Artificial Sequence
<220> FEATURE:
<223> OTHER INFORMATION: des Met(O)14 Asp28 Pro36, Pro37, Pro38
      Exendin-4(1-39)-NH2

<400> SEQUENCE: 29

His Gly Glu Gly Thr Phe Thr Ser Asp Leu Ser Lys Gln Glu Glu Glu
1               5                   10                  15

Ala Val Arg Leu Phe Ile Glu Trp Leu Lys Asp Gly Gly Pro Ser Ser
            20                  25                  30

Gly Ala Pro Pro Pro Ser
        35

<210> SEQ ID NO 30
<211> LENGTH: 44
<212> TYPE: PRT
<213> ORGANISM: Artificial Sequence
<220> FEATURE:
<223> OTHER INFORMATION: H-(Lys)6-desPro36, Pro37, Pro38 [Met(O)14,
      Asp28] Exendin-4(1-39)-NH2
<220> FEATURE:
<221> NAME/KEY: MISC_FEATURE
<222> LOCATION: (20)..(20)
<223> OTHER INFORMATION: X = methionine oxide

<400> SEQUENCE: 30

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser 35      40

<210> SEQ ID NO 31
<211> LENGTH: 44
<212> TYPE: PRT
<213> ORGANISM: Artificial Sequence
<220> FEATURE:
<223> OTHER INFORMATION: H-Asn-(Glu)5-des Pro36, Pro37, Pro38
    [Met(O)14, Asp28] Exendin-4(1-39)-NH2
<220> FEATURE:
<221> NAME/KEY: MISC_FEATURE
<222> LOCATION: (20)..(20)
<223> OTHER INFORMATION: X = methionine oxide

<400> SEQUENCE: 31

Asn Glu Glu Glu Glu Glu His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser
            35                  40

<210> SEQ ID NO 32
<211> LENGTH: 44
<212> TYPE: PRT
<213> ORGANISM: Artificial Sequence
<220> FEATURE:
<223> OTHER INFORMATION: des Pro36, Pro37, Pro38 [Met(O)14, Asp28]
    Exendin-4(1-39)-(Lys)6-NH2
<220> FEATURE:
<221> NAME/KEY: MISC_FEATURE
<222> LOCATION: (14)..(14)
<223> OTHER INFORMATION: X = methionine oxide

<400> SEQUENCE: 32

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser Lys Lys Lys Lys Lys Lys
            35                  40

<210> SEQ ID NO 33
<211> LENGTH: 50
<212> TYPE: PRT
<213> ORGANISM: Artificial Sequence
<220> FEATURE:
<223> OTHER INFORMATION: H-(Lys)6-des Pro36, Pro37, Pro38 [Met(O)14,
    Asp28] Exendin-4(1-39)-(Lys)6-NH2
<220> FEATURE:
<221> NAME/KEY: MISC_FEATURE
<222> LOCATION: (20)..(20)
<223> OTHER INFORMATION: X = methionine oxide

<400> SEQUENCE: 33

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
            35                  40                  45

Lys Lys
    50

<210> SEQ ID NO 34

```
<211> LENGTH: 50
<212> TYPE: PRT
<213> ORGANISM: Artificial Sequence
<220> FEATURE:
<223> OTHER INFORMATION: H-Asn-(Glu)5 des Pro36, Pro37, Pro38 [Met(O)14,
      Asp28] Exendin-4(1-39)-(Lys)6-NH2
<220> FEATURE:
<221> NAME/KEY: MISC_FEATURE
<222> LOCATION: (20)..(20)
<223> OTHER INFORMATION: X = methionine oxide

<400> SEQUENCE: 34

Asn Glu Glu Glu Glu Glu His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 35
<211> LENGTH: 50
<212> TYPE: PRT
<213> ORGANISM: Artificial Sequence
<220> FEATURE:
<223> OTHER INFORMATION: H-Lys6-des Pro36 [Met(O)14, Trp(O2)25, Asp28]
      Exendin-4(1-39)-Lys6-NH2
<220> FEATURE:
<221> NAME/KEY: MISC_FEATURE
<222> LOCATION: (20)..(20)
<223> OTHER INFORMATION: X = methionine oxide
<220> FEATURE:
<221> NAME/KEY: MISC_FEATURE
<222> LOCATION: (31)..(31)
<223> OTHER INFORMATION: X = tryptophan dioxide

<400> SEQUENCE: 35

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 36
<211> LENGTH: 38
<212> TYPE: PRT
<213> ORGANISM: Artificial Sequence
<220> FEATURE:
<223> OTHER INFORMATION: H-des Asp28 Pro36, Pro37, Pro38 [Met(O)14,
      Trp(O2)25] Exendin-4(1-39)-NH2
<220> FEATURE:
<221> NAME/KEY: MISC_FEATURE
<222> LOCATION: (14)..(14)
<223> OTHER INFORMATION: X = methionine oxide
<220> FEATURE:
<221> NAME/KEY: MISC_FEATURE
<222> LOCATION: (25)..(25)
<223> OTHER INFORMATION: X = tryptophan oxide

<400> SEQUENCE: 36

His Gly Glu Gly Thr Phe Thr Ser Asp Leu Ser Lys Gln Xaa Glu Glu
1               5                   10                  15

Glu Ala Val Arg Leu Phe Ile Glu Xaa Leu Lys Gly Gly Pro Ser Ser
```

Gly Ala Pro Pro Pro Ser
        35

<210> SEQ ID NO 37
<211> LENGTH: 44
<212> TYPE: PRT
<213> ORGANISM: Artificial Sequence
<220> FEATURE:
<223> OTHER INFORMATION: H-Asn-(Glu)5-des Pro36, Pro37, Pro38 [Met(O)14,
      Trp(O2)25, Asp28] Exendin-4(1-39)-NH2
<220> FEATURE:
<221> NAME/KEY: MISC_FEATURE
<222> LOCATION: (20)..(20)
<223> OTHER INFORMATION: X = methionine oxide
<220> FEATURE:
<221> NAME/KEY: MISC_FEATURE
<222> LOCATION: (31)..(31)
<223> OTHER INFORMATION: X = tryptophan oxide

<400> SEQUENCE: 37

Asn Glu Glu Glu Glu Glu His Gly Glu Gly Thr Phe Thr Ser Asp Leu
1               5                   10                  15

Ser Lys Gln Xaa Glu Glu Glu Ala Val Arg Leu Phe Ile Glu Xaa Leu
            20                  25                  30

Lys Asp Gly Gly Pro Ser Ser Gly Ala Pro Pro Ser
        35                  40

<210> SEQ ID NO 38
<211> LENGTH: 44
<212> TYPE: PRT
<213> ORGANISM: Artificial Sequence
<220> FEATURE:
<223> OTHER INFORMATION: des Pro36, Pro37, Pro38 [Met(O)14, Trp(O2)25,
      Asp28] Exendin-4(1-39)-(Lys)6-NH2
<220> FEATURE:
<221> NAME/KEY: MISC_FEATURE
<222> LOCATION: (14)..(14)
<223> OTHER INFORMATION: X = methionine oxide
<220> FEATURE:
<221> NAME/KEY: MISC_FEATURE
<222> LOCATION: (25)..(25)
<223> OTHER INFORMATION: X = tryptophan oxide

<400> SEQUENCE: 38

His Gly Glu Gly Thr Phe Thr Ser Asp Leu Ser Lys Gln Xaa Glu Glu
1               5                   10                  15

Glu Ala Val Arg Leu Phe Ile Glu Xaa Leu Lys Asp Gly Gly Pro Ser
            20                  25                  30

Ser Gly Ala Pro Pro Ser Lys Lys Lys Lys Lys Lys
        35                  40

<210> SEQ ID NO 39
<211> LENGTH: 50
<212> TYPE: PRT
<213> ORGANISM: Artificial Sequence
<220> FEATURE:
<223> OTHER INFORMATION: H-(Lys)6-des Pro36, Pro37, Pro38 [Met(O)14,
      Trp(O2)25, Asp28] Exendin-4(S1-39)-(Lys)6-NH2
<220> FEATURE:
<221> NAME/KEY: MISC_FEATURE
<222> LOCATION: (20)..(20)
<223> OTHER INFORMATION: X = methionine oxide
<220> FEATURE:
<221> NAME/KEY: MISC_FEATURE
<222> LOCATION: (31)..(31)
<223> OTHER INFORMATION: X = tryptophan oxide

<400> SEQUENCE: 39

-continued

```
Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Xaa Leu
                20                  25                  30

Lys Asp Gly Gly Pro Ser Ser Gly Ala Pro Pro Ser Lys Lys Lys Lys
            35                  40                  45

Lys Lys
    50

<210> SEQ ID NO 40
<211> LENGTH: 50
<212> TYPE: PRT
<213> ORGANISM: Artificial Sequence
<220> FEATURE:
<223> OTHER INFORMATION: H-Asn-(Glu)5-des Pro36, Pro37, Pro38 [Met(O)14,
      Trp(O2)25, Asp28] Exendin-4(1-39)-(Lys)6-NH2
<220> FEATURE:
<221> NAME/KEY: MISC_FEATURE
<222> LOCATION: (20)..(20)
<223> OTHER INFORMATION: X = methionine oxide
<220> FEATURE:
<221> NAME/KEY: MISC_FEATURE
<222> LOCATION: (31)..(31)
<223> OTHER INFORMATION: X = tryptophan oxide

<400> SEQUENCE: 40

Asn Glu Glu Glu Glu His Gly Glu Gly Thr Phe Thr Ser Asp Leu
1               5                   10                  15

Ser Lys Gln Xaa Glu Glu Glu Ala Val Arg Leu Phe Ile Glu Xaa Leu
                20                  25                  30

Lys Asp Gly Gly Pro Ser Ser Gly Ala Pro Pro Ser Lys Lys Lys Lys
            35                  40                  45

Lys Lys
    50
```